United States Patent [19]

Rösner et al.

[11] 4,156,778
[45] May 29, 1979

[54] SUBSTITUTED BIS-BENZIMIDAZOLYL COMPOUNDS; PREPARATION AND USE THEREOF

[75] Inventors: Manfred Rösner, Eppstein; Heinz Loewe, Kelkheim; Wolfgang Raether, Dreieich, all of Fed. Rep. of Germany

[73] Assignee: Hoechst Aktiengesellschaft, Frankfurt am Main, Fed. Rep. of Germany

[21] Appl. No.: 886,517

[22] Filed: Mar. 14, 1978

[30] Foreign Application Priority Data

Mar. 16, 1977 [DE] Fed. Rep. of Germany ....... 2711362
Feb. 4, 1978 [DE] Fed. Rep. of Germany ....... 2804835

[51] Int. Cl.² ............................................. C07D 235/20
[52] U.S. Cl. ................................... 544/296; 548/328; 424/251; 424/273 R
[58] Field of Search ...................... 544/296; 548/328; 424/273, 251

[56] References Cited

U.S. PATENT DOCUMENTS

| | | | |
|---|---|---|---|
| 2,733,244 | 1/1956 | Synerholm et al. | 548/347 |
| 2,995,564 | 8/1961 | Duennenberger | 548/328 |
| 3,103,518 | 9/1963 | Duennenberger | 548/328 |
| 3,179,669 | 4/1965 | Ursprung | 548/328 |
| 3,287,469 | 11/1966 | Harvey, Jr. | 548/347 |
| 3,337,578 | 8/1967 | Bader et al. | 548/328 |
| 3,971,782 | 7/1976 | White et al. | 548/347 |
| 3,992,403 | 11/1976 | Roebke | 548/347 |

OTHER PUBLICATIONS

Wright Chem. Rev. 1951, vol. 48, pp. 431 & 444–446.
Ciba Chem. Abst. 1949, vol. 43, col. 5194 (5194f); col. 8145.
Lisunova et al., Chem. Abst. 1975, vol. 75, No. 43323p.

*Primary Examiner*—Alan L. Rotman
*Attorney, Agent, or Firm*—Curtis, Morris & Safford

[57] ABSTRACT

Substituted bis-benzimidazolyl compounds of the formula

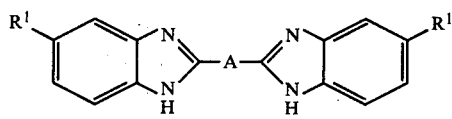

are disclosed, wherein A is thiophenediyl, furanediyl, phenylene, or phenoxyphenylene, and $R^1$ is

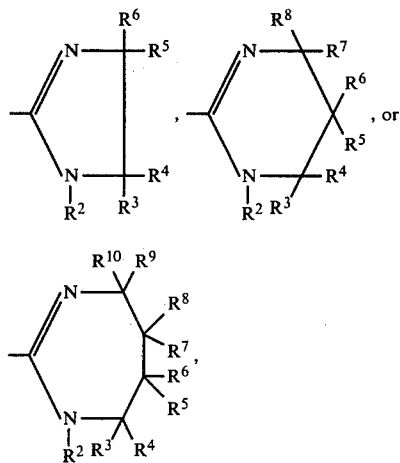

where $R^2$–$R^{10}$ are independently hydrogen, alkyl, aminoalkyl, N-alkylaminoalkyl, N,N-dialkylaminoalkyl, or phenyl, or any two of $R^2$–$R^{10}$ taken together are $C_2$–$C_4$ alkylene, as are methods of making the compounds, which are useful as chemotherapeutic agents in the treatment of protozoal and viral diseases.

1 Claim, No Drawings

SUBSTITUTED BIS-BENZIMIDAZOLYL COMPOUNDS; PREPARATION AND USE THEREOF

The present invention relates to substituted bis-benzimidazolyl compounds of the general formula I

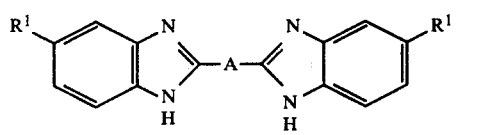

and the physiologically acceptable salts thereof, wherein A is 2,5-thiophenediyl, 2,5-furanediyl, p-phenylene, m-phenylene or 4,4'-phenoxyphenylene and wherein $R^1$ is a substituent selected from the general formulae IIa to IIc:

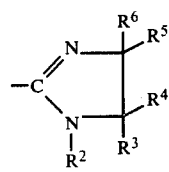

(IIa)

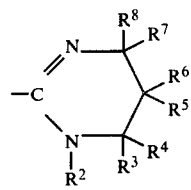

(IIb)

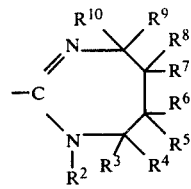

(IIc)

wherein in turn the radicals $R^2$ to $R^{10}$, independently from one another, are hydrogen, alkyl having 1–4 carbon atoms such as methyl, ethyl, n-propyl, iso-propyl, n-butyl, iso-butyl, tert.butyl, amino alkyl, N-alkylaminoalkyl, N,N-dialkylaminoalkyl, wherein each alkyl group has 1 to 4 carbon atoms, such as aminomethyl, aminoethyl, N-methylaminoethyl, N,N-dimethylaminoethyl, N,N-diethylaminopropyl, N,N-dibutylaminoethyl, or phenyl, and wherein two of the radicals $R^2$ to $R^{10}$ together may represent an alkylene bridge having 2, 3 or 4 carbon atoms.

Among the compounds of formula I preference is given to those wherein A means 2,5-thiophenediyl, 2,5-furanediyl, p-phenylene or 4,4'-phenoxyphenylene, and wherein the substituents $R^2$ to $R^{10}$ of the general formulae IIa to IIc are hydrogen, alkyl having 1 to 4, especially 1 to 2 carbon atoms or wherein two of the $R^2$ to $R^{10}$ radicals together are an alkylene bridge having 3 or 4 carbon atoms.

Especially preferred compounds of general formula I are those wherein A is 2,5-thiophenediyl, 2,5-furanediyl or p-phenylene, $R^2$ is hydrogen or methyl, $R^3$ to $R^{10}$ are hydrogen, alkyl having 1 to 4, especially 1 to 2 carbon atoms or wherein two of these radicals combined are an alkylene bridge having 3 or 4 carbon atoms, especially bridging two adjacent carbon atoms, and wherein only one, two or three of the radicals $R^2$ to $R^{10}$ are different from hydrogen.

A further subject of the present invention is a process for preparing substituted bis-benzimidazolyl compounds of formula I, which comprises reacting (a) a compound of formula III, $$R^{11}-A-R^{11} \quad \text{(III)}$$

wherein A has the meanings given for formula I, wherein $R^{11}$ is

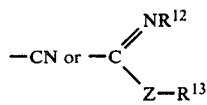

wherein in turn Z is O, S, NH or $NR^{12}$ $R^{12}$ being hydrogen or alkyl with 1 to 4 carbon atoms and $R^{13}$ being alkyl or alkoxyalkyl with 1 to 4 carbon atoms each per alkyl radical, especially methyl, ethyl, n-propyl, i-propyl, n-butyl or 2-methoxyethyl, with a compound of formula IV

(IV)

wherein $R^1$ has the meaning given for formulae IIa to IIc, or (b) reacting a compound of general formula V,

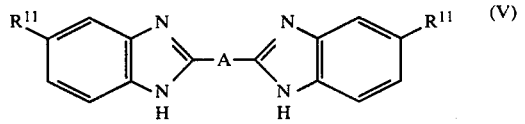

(V)

wherein A has the meanings given for formula I and wherein $R^{11}$ has the meanings given for formula III sub (a), with a diamine of one of the formulae VIa to VIc

(VIa)

(VIb)

(VIc)

wherein $R^2$ to $R^{10}$ have the meanings given for formulae IIa to IIc, and optionally converting the resulting compound of formula I into its salt by adding a physiologically acceptable acid HX, or converting the resulting salt of formula I into a compound of formula I by adding a base such as ammonia or sodium hydroxide solution.

In order to perform the process according to (a), a compound of formula III is reacted with a compound of formula IV (a₁) If $R^{11}$ represents —CN in formula III, the reaction is carried out with the addition of sulfur or sulfur-containing compounds such as hydrogen sulfide, alkali(poly)sulfides or ammonium (poly) sulfides either without solvent or in an inert solvent such as benzene, toluene, xylene, petroleum ether, ligroin, chloroform, carbon tetrachloride, dioxane or tetrahydrofurane. The reaction temperatures vary from 60 to 180° C., preferably from 80 to 140° C. The reaction time, depending on the reaction temperatures, varies from 1 to 10 hours.

(a₂) If $R^{11}$ in formula III is

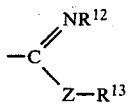

the reaction is suitably carried out in a polar solvent, in the presence of physiologically acceptable acid HX.

The reaction temperatures may vary from 0° to 180° C., preferably from 20° to 120° C., generally operating at the boiling temperature of the solvent employed.

Depending on the given conditions, the reaction times vary from 30 minutes to 5 hours. Preferred polar solvents are alcohols such as methanol, ethanol, isopropanol, n-propanol, n-butanol, iso-butanol or carboxylic acids such as formic acid, acetic acid, propionic acid.

Acids HX in consideration are mineral or organic acids, such as hydrochloric acid, hydrobromic acid, hydroiodic acid, phosphoric acid, acetic acid, propionic acid, benzoic acid, citric acid, maleic acid, malonic acid, lactic acid, tartaric acid, embonic acid, oxalic acid, fumaric acid, succinic acid, 2-hydroxyethane-sulfonic acid, acetylglycine.

A preferred embodiment of the process according to (a₂) is the operation with hydrochlorides of imidic acid esters, $R^{11}$ of formula III having the meaning

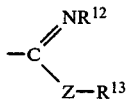

wherein Z stands for oxygen and $R^{12}$ and $R^{13}$ have the meanings given for formula III. Preferred solvents are in that case the alcohols indicated in (a₂).

For carrying out the process (b), a compound of formula V is reacted with a compound of formulae VIa to VIc. The reaction conditions, especially in view to the temperatures, presence or absence of solvents and reaction times, correspond to the conditions stated for carrying out the process (a), i.e. depending on the meaning of the radical $R^{11}$ in formula V, the process is carried out according to (a₁) or (a₂).

The aromatic diamines of formula IV are prepared according to known processes (cf. Houben-Weyl, Methoden der organischen Chemie, Vol. 11/1, p. 360 et seq.) by reducing a substituted nitro compound of formula VII,

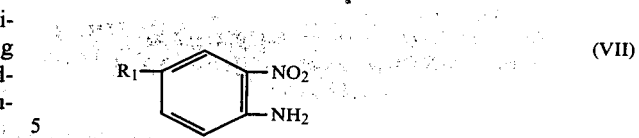

wherein $R^1$ has the meanings given for formulae IIa–IIc, for example by catalytic hydrogenation with Raney nickel.

The nitro compounds of formula VII are prepared by reacting a compound of formula VIII,

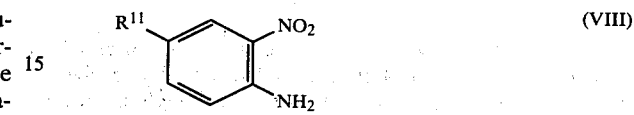

wherein $R^{11}$ has the meaning given for formula III, with a diamine of formulae VIa to VIc. The reaction conditions correspond to those stated for carrying out the process (a).

The compounds of the general formulae III, V and VIII are prepared by reacting a compound of formula III, wherein $R^{11}$ is —CN, with an alcohol $R^{13}$—OH and hydrogen chloride (cf. A. Pinner, "Die Iminoäther und ihre Derivate", Berlin 1892) to yield the imidic acid ester hydrochloride wherein $R^{11}$ is

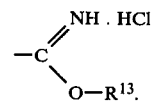

The other compounds of formula III are prepared from an imidic acid ester hydrochloride according to known processes by reaction with a compound of formula IX $$R^{13}-Z-H \qquad (IX)$$

wherein $R^{13}$ and Z have the meanings given for formula III, suitably at the boiling temperature of one of the alcohols specified in process (a₂).

Suitable diamines of formulae VIa to VIc are e.g.: ethylene diamine, 1,2-diaminopropane, 1,3-diaminopropane, 1,4-diaminobutane, 2,3-diaminobutane, 2,3-diamino-2,3-dimethyl butane, 1,2-diaminobutane, 1,3-diamino-2,2-dimethyl-(diethyl, dipropyl, dibutyl-)-propane, 1,2-diaminocyclohexane, 1-amino-2-aminomethylcyclopentane, N-methylethylene-diamine, N-methylpropylene-diamine.

Upon reacting the aromatic diamines of formula IV with compounds of general formula III, the substituent $R^1$ in the product of general formula I may take the 5- or 6-position in the benzimidazole ring. However, due to the tautomeric properties of the imidazole ring and due to the free rotation between imidazole portion and bridge portion A, the result is one single substituted bis-benzimidazolyl compound each time. Therefore, the compounds claimed in formula I include all the tautomers and mixtures thereof.

In analogy, the same applies to the substituents $R^3$ to $R^{10}$ in the formulae IIa to IIc, if $R^2$ is hydrogen and if at least one of the radicals $R^3$ to $R^{10}$ is different from hydrogen. If the compounds of formulae I, IV, VIa to VIc and VII are present as stereoisomers due to their substitution, all such enantiomers, diastereomers and mixtures thereof and racemic compounds are included in the scope of the invention.

The substituted bis-benzimidazolyl compounds according to the present invention are chemotherapeutics and well suitable for treating parasitic infections, especially protozoal and virus diseases in human beings and animals.

They are especially efficient against diseases induced by trypanosomae such as trypanosoma brucei, trypanosoma rhodesiense, trypanosoma gambiense, trypanosoma evansi, trypanosoma equinum, trypanosoma equiperdum, trypanosoma congolense, or trypanosoma vivax.

The compounds of formula I are especially suitable as the active ingredients in compositions used in veterinary medicine. The compounds of the invention are especially distinguished by a large range of action, particularly against medicine-resistant strains of the afore mentioned trypanosomae, by a low dosis curativa minima and a good compatibility.

The active substances are administered orally or parenterally, combined with suitable pharmaceutical solvents or carriers, preference of one or the other of the possible administration forms depending on the circumstances. For that purpose there may be considered for example tablets, capsules, solutions or suspensions.

The following Examples illustrate the invention:

EXAMPLE 1

Manufacture of the starting materials (Process a)

Thiophene-2,5-dicarboximidic acid-diethyl ester-dihydrochloride = TDD (Formula III)

30 g of thiophene-2,5-dicarboxylic acid nitrile are dissolved in 160 ml of dioxane. After the addition of 30 ml of ethanol, gaseous hydrochloric acid is introduced till saturation, while maintaining the temperature of the solution below 20° C. The suspension formed is stirred with ether for 24 hours, filtered off with suction, washed with ether and dried over KOH in a desiccator.

Yield: 64 g (corresponding to 95.5% of the theoretical yield) Melting point above 300° C.

In analogous manner is prepared:

Furane-2,5-dicarboximidic acid diethyl ester-dihydrochloride = FDD
(Formula III), Melting point 126°–127° C., decomposition, from furane-2,5-dicarboxylic acid nitrile.

Terephthalimidic acid-bis(2-methoxyethyl)-ester-dihydrochloride = TIB (Formula III)

50 g of terephthalic acid dinitrile are dissolved in 500 ml of 2-methoxyethanol. Gaseous hydrochloric acid is introduced till saturation, while maintaining the temperature of the solution below 20° C. The suspension formed is agitated with ether, filtered off with suction, washed with ether and dried over KOH in a desiccator.

Yield: 135 g (97.9% theor. yield),
Melting point above 300° C.

In analogous manner is prepared:
Isophthalimidic acid-bis-(2-methoxyethyl-ester-dihydrochloride = IIB (Formula III)
Melting point 141° C. with decomposition, from isophthalic acid dinitrile.

4,4'-bis-(2-methoxyethoxycarbonimidoyl)-diphenylether-dihydro-chloride = BMD (Formula III)

50 g of 4,4'-dicyanodiphenylether are suspended in 500 ml of 2-methoxyethanol. Gaseous hydrochloric acid is introduced, the temperature is allowed to rise to 70° C., and this temperature is maintained by cooling until it decreases by itself. The solution is allowed to stand overnight, it is then concentrated in vacuo at max. 45° C. and acetone is added. The precipitate is filtered off with suction, washed with acetone and dried over KOH in a desiccator.

Yield: 88 g (87.1% of theor. yield),
Melting point 101°–103° C.

4-Amino-3-nitrobenzimidic acid-(2-methoxyethyl)-ester-hydrochloride = ANB (Formula VIII)

100 g of 4-amino-3-nitrobenzonitrile are suspended in 500 ml of 2-methoxyethanol. Gaseous hydrochloric acid is introduced, the temperature of the solution is allowed to rise to 70° C. in the course of the introduction, and the solution is maintained at this temperature by cooling until it decreases by itself. Finally, the solution is cooled to 0°–5° C., saturated with gaseous hydrochloric acid and allowed to stand overnight. The precipitate is then filtered off with suction, washed with isopropanol and dried over KOH in a desiccator.

Yield: 155.8 g (corresponding to 92% of the theor. yield),
Melting point 220° C.

2-(4-amino-3-nitrophenyl)-4(5)-methyl-2-imidazoline-hydrochloride (Formula VII)

22.5 g of 1,2-diaminopropane and 82.7 g of 4-amino-3-nitrobenzimidic acid-(2-methoxyethyl)-ester-hydrochloride are agitated under reflux in 300 ml of ethanol for three hours.

The solution is brought to dryness under reduced pressure, dissolved in 100 ml of water, treated with activated charcoal, filtered and mixed with 100 ml of concentrated hydrochloric acid.

The precipitated hydrochloride is recrystallized from methanol.

Yield: 71.6 g (corresponding to 93% of theor. yield),
Melting point 125° (with decomposition)

2-(3,4-diaminophenyl)-4(5)-methyl-2-imidazoline-hydrochloride (Formula IV)

51 g of 2-(4-amino-3-nitrophenyl)-4(5)-methyl-2-imidazoline-hydrochloride are hydrogenated in 1 l of methanol with Raney-nickel at room temperature. After termination of the hydrogen absorption, the catalyst is filtered off with suction and the filtrate is brought to dryness under reduced pressure. The remaining oil is recrystallized from isopropanol. Yield: 42.6 g (corresponding to 94% of theor. yield),
Melting point 209°211° C.

Manufacture of the final products (Process a)

2,5-bis-[5(6)-(4(5)-methyl-2-imidazoline-2-yl)-2-benzimidazolyl]-thiophene-tetrahydrochloride (Formula I)

9.1 g of 2-(3,4-diaminophenyl)-4(5)-methyl-2-imidazoline-hydrochloride and 6 g of thiophene-2,5-dicarboximidic acid diethyl ester-dihydrochloride are stirred under reflux in 50 ml of methanol for 3 hours and subsequently brought to dryness under reduced pressure. The residue is dissolved in 50 ml of 2N hydrochloric acid, while still hot, treated with activated charcoal, filtered and mixed with 50 ml of concentrated hydrochloric acid.

Upon cooling, the tetrahydrochloride crystallizes.
Yield: 10.5 g (corresponding to 84% of theor. yield)
Melting point 300°302° C. (decompos.)

For preparing the free base, the tetrahydrochloride is dissolved in water and at the boiling point of the solution mixed with aqueous ammonia. The free base as precipitated melts above 320° C.

By adding at least equimolar quantities of a physiologically acceptable acid, the aforementioned free base yields the corresponding salt, e.g. the acetate, maleate or aceturate.

The following compounds of formula I are prepared by analogous processes:

From 2-(3,4-diaminophenyl)-(4(5)-methyl-2-imidazoline-hydrochloride (see Example 1) (Formula IV) with 2. FDD
2,5-bis-[5(6)-(4(5)-methyl-2-imidazolin-2-yl)-benzimidazolyl]-furane-hydrobromide, (melting point above 300° C.), is obtained, 3. TIB
1,4-bis-[5(6)-(4(5)-methyl-2-imidazoline-2-yl)-2-benzimidazolyl]-benzene-hydrochloride, (melting point above 300° C.), is obtained, 4. IIB
1,3-bis-[5(6)-(4(5)-methyl-2-imidazoline-2-yl)-2-benzimidazolyl]-benzene-hydrobromide (melting point above 300° C.), is obtained, 5. BMD
4,4'-bis-[5(6)-4(5)-methyl-2-imidazolin-2-yl)-2-benzimidazolyl]-diphenyl ether-hydrobromide, (melting point above 300° C.), is obtained.

From ethylene diamine through 2-(4-amino-3-nitro-phenyl)-2-imidazoline-hydrochloride (melting point 213° C.) and 2-(3,4-diaminophenyl)-2-imidazoline-hydrochloride (melting point 220° C.) with 6. TDD
2,5-bis[5(6)-(2-imidazoline-2-yl)-2-benzimidazolyl]-thiophene-hydrochloride, (melting point 306° C.), is obtained, 7. FDD
2,5-bis-[5(6)-2-imidazoline-2-yl)-2-benzimidazolyl]-furane-hydrobromide, (melting point above 300° C., is obtained, 8. TIB
1,4-bis-[5(6)-(2-imidazoline-2-yl)-2-benzimidazolyl]-benzene-hydrochloride, (melting point above 300° C.) is obtained, 9. IIB
1,3-bis-[5(6)-(2-imidazoline-2-yl)-2-benzimidazolyl]-benzene-hydrochloride, (melting point above 300° C.), is obtained, 10. BMD
4,4'-bis-[5(6)-(2-imidazoline-2-yl)-2-benzimidazolyl]-diphenylether-hydrochloride, (melting point above 300° C.), is obtained.

From 1,3-diaminopropane through 2-(4-amino-3-nitrophenyl)-2-tetrahydropyrimidine-hydrochloride, (melting point 280° C.), and 2-(3,4-diaminophenyl)-2-tetrahydropyrimidine-hydrochloride, (melting point above 300° C.) with 11. TDD
2,5-bis-[5(6)-(2-tetrahydropyrimidine-2-yl)-2-benzimidazolyl]-thiophene-hydrochloride, (melting point 270° C.), is obtained, 12. FDD
2,5-bis-[5(6)-(2-tetrahydropyrimidine-2-yl)-2-benzimidazolyl]-furane-hydroiodide, (melting point above 300° C.), is obtained, 13. TIB
1,4-bis-[5(6)-(2-tetrahydropyrimidine-2-yl)-2-benzimidazolyl]-benzene-hydrochloride, (melting point above 300° C.), is obtained, 14. IIB
1,3-bis-[5(6)-(2-tetrahydropyrimidine-2-yl)-2-benzimidazolyl]-benzene-hydrobromide, (melting point above 300° C.), is obtained, 15. BMD
4,4'-bis-[5(6)-(2-tetrahydropyrimidine-2-yl)-2-benzimidazolyl]-diphenylether-hydroiodide, (melting point above 300° C.), is obtained.

16. From 1,3-diamino-2,2-dimethylpropane through 2-(4-amino-3-nitro-phenyl)-5,5-dimethyl-2-tetrahydropyrimidine-hydrochloride (melting point 280° C.) and 2-(3,4-diaminophenyl)-5,5-dimethyl-2-tetrhydropyrimidinehydrochloride (melting point 240°-245° C.) with TDD
2,5-bis-[5(6)-(5,5-dimethyl-2-tetrahydropyrimidine-2-yl)-2-benzimidazolyl]-thiophene-hydrochloride, (melting point above 300° C.), is obtained, From 1-amino-2-aminomethyl-2-propyl-pentane through 2-(4-amino-3-nitrophenyl)-5,5-dipropyl-2-tetrahydropyrimidine-hydrochloride (melting point 273° C.) and 2-(3,4-diaminophenyl)-4,5-dipropyl-2-tetrahydropyrimidine-hydrochloride (melting point 228° C.) with 17. TDD
2,5-bis-[5(6)-(5,5-dipropyl-2-tetrahydropyrimidine-2-yl)-2-benzimidazolyl]-thiophene-hydrochlorie, (melting point 257° C.), is obtained.

18. BMD
4,4'-bis-[5(6)-(5,5-dipropyl-2-tetrahydropyrimidine-2-yl)-2-benzimidazolyl]-diphenylether-hydrochloride, (melting point above 300° C.), is obtained.

19. From 1,4-diaminobutane through 2-(4-amino-3-nitrophenyl)-(1H-4,5,6,7-tetrahydro-1,3-diazepine)-hydroiodide (melting point 279°-280° C.), and 2-(3,4-diaminophenyl)-(1H-4,5,6,7-tetrahydro-1,3-diazepine)-hydroiodide with TDD
2,5-bis-[5(6)-(1H-4,5,6,7-tetrahydro-1,3-diazepine-2-yl)-2-benzimidazolyl]-thiophene-hydroiodide, (melting point above 300° C.), is obtained.

20. From N-methylpropylenediamine through 2-(4-amino-3-nitro-phenyl)-1-methyl-2-tetrahydropyrimidine-hydrochloride (melting point 248° C.) and 2-(3,4-diaminophenyl)-1-methyl-2-tetrahydropyrimidine-hydrochloride (melting point 274° ) with TDD
2,5-bis-[5(6)-(1-methyl-2-tetrahydropyrimidine-2-yl)-2-benzimidazolyl]-thiophene-hydrobromide, (melting point above 300° C.), is obtained.

21. From diethylenetriamine through 1-aminoethyl-2-(4-amino-3-nitro-phenyl)-2-imidazoline-hydroiodide (melting point 289° C., decomp.) and 1-aminoethyl-2-(3,4-diaminophenyl)-2-imidazoline-hydroiodide with TDD
2,5-bis-[5(6)-(1-aminoethyl-2-imidazoline-2-yl)-2-benzimidazolyl]-thiophene-hydroiodide, (melting point above 300° C.), is obtained.

From 2,3-diaminobutane through 2-(4-amino-3-nitrophenyl)-4,5-dimethyl-2-imidazoline-hydrochloride, (melting point 225° C.), and 2-(3,4-diaminophenyl)-4,5-dimethyl-2-imidazoline-hydrochloride (melting point 236°-238° C.) with

22. TDD 2,5-bis-[5(6)-(4,5-dimethyl-2-imidazoline-2-yl)-2-benzimidazolyl]-thiophene-hydrobromide, (melting point above 300° C.), is obtained, 23. FDD
2,5-bis-[5(6)-(4,5-dimethyl-2-imidazoline-2-yl)-2-benzimidazolyl]-furane-hydroiodide, (melting point 270° C., decomp.), is obtained, 24. TIB
1,4-bis-[5(6)-(4,5-dimethyl-2-imidazoline-2-yl)-2-benzimidazolyl]-benzene-hydrochloride, (melting point above 300° C.) is obtained, 25. IIB
1,3-bis-[5(6)-(4,5-dimethyl-2-imidazoline-2-yl)-2-benzimidazolyl]-benzene-CH₃COOH, (melting point 200° C. decomp.), is obtained, 26. BMD
4,4'-bis-[5(6)-(4,5-dimethyl-2-imidazoline-2-yl)-2-benzimidazolyl]-diphenylether-hydroiodide, (melting point above 300° C.), is obtained.

From 1,2-diaminobutane through 4(5)-ethyl-2-(4-amino-3-nitro-pheny)-2-imidazoline-hydroiodide, (melting point 219°220° C.) and 4(5)-ethyl-2-(3,4-diaminophenyl)-2-imidazoline-hydroiodide (melting point 154°155° C. decomp.) with 27. TDD
2,5-bis-[5(6)-(4(5)-ethyl-2-imidazoline-2-yl)-2-benzimidazolyl]-thiophene-hydrobromide, (melting point 263° C. decomp.), is obtained, 28. FDD
2,5-bis-[5(6)-(4(5)-ethyl-2-imidazoline-2-yl)-2-benzimidazolyl]-furane-hydroiodide, (melting point 240°243° C. decomp.), is obtained, 29. TIB
1,4-bis-[5(6)-(4(5)-ethyl-2-imidazoline-2-yl)-2-benzimidazolyl]-benzene-hydrochloride, (melting point above 300° C.), is obtained, 30. IIB
1,3-bis-[5(6)-(4(5)-ethyl-2-imidazoline-2-yl)-2-benzimidazolyl]-benzene-hydroiodide, (melting point 225° C. decomp.), is obtained, 31. BMD
4,4'-bis-[5(6)-(4(5)-ethyl-2-imidazoline-2-yl)-2-benzimidazolyl]-diphenylether-CH₃COOH, (melting point 175° C. decomp.), is obtained.

32. From 1,2-diaminocyclohexane through 2-(4-amino-3-nitrophenyl)-4,5-tetramethylene-2-imidazoline-hydrochloride (melting point 230° C.) and 2-(3,4-diaminophenyl)-4,5-tetramethylene-2-imidazoline-hydrochloride (melting point 248°–250° C. decomp.) with TDD 2,5-bis-[5(6)-(4,5-tetramethylene-2-imidazoline-2-yl)-2-benzimidazolyl]-thiophene-hydrochloride, (melting point above 300° C.) is obtained.

From 1-amino-2-aminomethylcyclopentane through 2-(4-amino-3-nitrophenyl)-4,5-(5,6)-trimethylene-2-tetrahydropyrimidine-hydroiodide (melting point 243°–244° C.) and 2-(3,4-diaminophenyl)-4,5-(5,6)-trimethylene-2-tetrahydropyrimidine-hydroiodide with 33. TDD
2,5-bis-[5(6)-(4,5(5,6)-trimethylene-2-tetrahydropyrimidine-2-yl)-2-benzimidazolyl]-thiophene-hydrobromide, (melting point 265° C.), is obtained.

34. TIB
1,4-bis-[5(6)-(4,5(5,6)-trimethylene-2-tetrahydropyrimidine-2-yl)-2-benzimidazolyl]-benzene-hydrochloride, (melting point above 300° C.), is obtained.

From N-methylethylenediamine through 2-(4-amino-3-nitrophenyl)-1-methyl-2-imidazoline-hydrochloride (melting point 252°–253° C.) and 2-(3,4-diaminophenyl)-1-methyl-2-imidazoline-hydrochloride (melting point 288°–290° C.) with 35. TIB
1,4-bis-[5(6)-(1-methyl-2-imidazoline-2-yl)-2-benzimidazolyl]-benzene-hydroiodide, (melting point above 300° C.), is obtained.

36. IIB
1,3-bis-[5(6)-(1-methyl-2-imidazoline-2-yl)-2-benzimidazolyl]-benzene-hydroiodide, (melting point 220° C. decomp.), is obtained, 37. BMD
4,4'-bis-[5(6)-(1-methyl-2-imidazoline-2-benzimidazolyl]-diphenylether-CH₃COOH, (melting point 115° C. decomp.), is obtained.

EXAMPLE 38

Manufacture of the starting materials (Process b)

2,5-bis-(5(6)-cyano-2-benzimidazolyl)-thiophene (Formula V)

30 g of thiophene-2,5-dicarboximidic acid diethyl esterdihydrochloride are boiled under reflux for 4 hours in 250 ml of methanol with 26.7 g of 3,4-diaminobenzonitrile. The precipitate formed is filtered off with suction, washed with water and recrystallized from 800 ml of methyl glycol. Yield: 30.5 g (corresponding to 83.3% of theor. yield), melting point above 300° C.

2,5-bis[5(6)-(2-methoxyethoxycarbonimidoyl)-2-benzimidazolyl]-thiophene-tetrahydrochloride (Formula V)

15.5 g of 2,5-bis-(5(6)-cyano-2-benzimidazolyl)-thiophene are suspended in 155 ml of 2-methoxyethanol. Gaseous HCl is introduced till saturation, while the temperature of the solution is maintained below 20° C.

The suspension formed is stirred with ether after 24 hours, filtered off with suction, washed with ether and dried over KOH in a desiccator.

Yield: 26.3 g (corresponding to 93.6% of theor. yield), melting point 273° C. (decompos.)

Manufacture of the final products (Process b)

2,5-bis-[5(6)-(1-methyl-2-imidazoline-2-yl)-2-benzimidazolyl]-thiophene-tetrahydrochloride (Formula I)

7.5 g of N-methylethylene diamine and 6.6 g of 2,5-bis [5(6)-(2-methoxyethoxy-carbonimidoyl)-2-benzimidazolyl]-thiophene-tetrahydrochloride are stirred under reflux for 3 hours in 70 ml of methanol and subsequently brought to dryness under reduced pressure. The residue is dissolved in 50 ml of 2N-hydrochloric acid while still hot, treated with activated charcoal and filtered. Tetrahydrochloride is crystallizing upon cooling.

Yield: 4.9 g (corresponding to 79% of theor. yield), melting point 259° C. (decomposition).

What is claimed is:

1. A substituted bis-benzimidazolyl compound of the formula

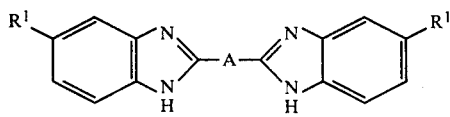

or a physiologically acceptable salt thereof, wherein A is 2,5-thiophenediyl, 2,5-furanediyl, p-phenylene, m-phenylene or 4,4'-phenoxyphenylene, and wherein $R^1$ is

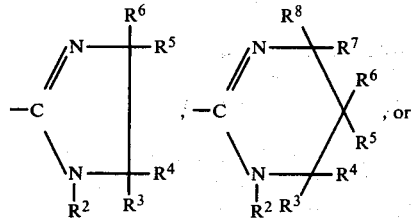

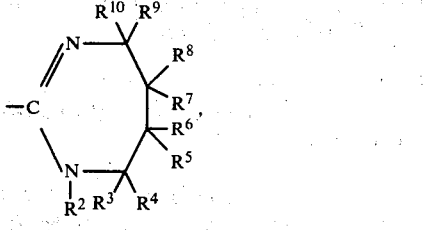

wherein in turn the radicals $R^2$ to $R^{10}$, independently of one another, are hydrogen, alkyl having 1–4 carbon atoms, aminoalkyl, N-aminoalkyl, or N,N-dialkylaminoalkyl wherein each alkyl has from 1 to 4 carbon atoms each, or phenyl, or wherein two of the radicals $R^2$ to $R^{10}$ together are an alkylene bridge having 2, 3 or 4 carbon atoms.

* * * * *